United States Patent [19]
Motoyama et al.

[11] Patent Number: 5,980,780
[45] Date of Patent: Nov. 9, 1999

[54] RACEMIC COMPOUND AND ANTI-FERROELECTRIC LIQUID CRYSTAL COMPOSITION CONTAINING THE COMPOUND

[75] Inventors: Yuki Motoyama; Takahiro Matsumoto; Tomoyuki Yui; Masahiro Johno, all of Tsukuba, Japan

[73] Assignee: Mitsubishi Gas Chemical Company, Inc., Tokyo, Japan

[21] Appl. No.: 09/055,211

[22] Filed: Apr. 6, 1998

[51] Int. Cl.⁶ .......................... C09K 19/20; C09K 19/21
[52] U.S. Cl. ................. 252/299.64; 252/299.65; 252/299.66; 252/299.67
[58] Field of Search .............. 252/299.01, 299.64, 252/299.65, 299.66, 299.67; 349/174

[56] References Cited

U.S. PATENT DOCUMENTS

| | | | |
|---|---|---|---|
| 4,780,242 | 10/1988 | Miyazawa et al. | 252/299.65 |
| 5,716,542 | 2/1998 | Iwaya et al. | 252/299.61 |

FOREIGN PATENT DOCUMENTS

| | | |
|---|---|---|
| 0110299 | 6/1984 | European Pat. Off. |
| 0136725 | 4/1985 | European Pat. Off. |
| 0194659 | 9/1986 | European Pat. Off. |
| 0829469 | 3/1998 | European Pat. Off. |
| 62-273284 | 11/1987 | Japan . |
| 1-213390 | 8/1989 | Japan . |

OTHER PUBLICATIONS

Murashiro et al., "Dopant effect on threshold electric field of antiferroelectric liquid crystal switching", Liquid Crystal Vo. 14(2), 371–380, 1993.
WPIDS 88–010482, 1988.
WPIDS 89–289849, 1989.
Chandani, et al., "Tristable Switching in Surface Stabilized Ferroelectric Liquid Crystals with a Large Spontaneous Polarization", Jap. Journal of Applied Physics, vol. 27, No. 5, May 1988, pp. L729–L732.
Chandani, et al., "Novel Phases Exhibiting Tristable Switching", Jap. Journal of Applied Physics, vol. 28, No. 7, Jul. 1989, pp. L1261–L1264.
Chandani, et al., "Antiferroelectric Chiral Smectic Phases Responsible for the Tristable Switching in MHPOBC", Jap. Journal of Applied Physics, vol. 28, No. 7, Jul. 1989, pp. L1265–L1268.
Johno, et al., "Smectic Layer Switching by an Electric Field in Ferroelectric Liquid Crystal Cells", Jap. Journal of Applied Physics, vol. 28, No. 1, Jan. 1989, pp. L119–L120.
Johno, et al., "Correspondence between Smectic Layer Switching and DC Hysteresis of Apparent Tilt Angle in an Antiferroelectric Liquid Crystal Mixture", Jap. Journal of Applied Physics, vol. 29, No. 1, Jan. 1990, pp. L111–L114.
Yamamoto, et al., "Full–Color Antiferrelectric Liquid Crystal Display", Preprints—4th International Conference on Ferroelectric Liquid Crystals–1993, pp. 77–78.

*Primary Examiner*—Shean C. Wu
*Attorney, Agent, or Firm*—Sherman and Shalloway

[57] ABSTRACT

A racemic compound of the formula (1)

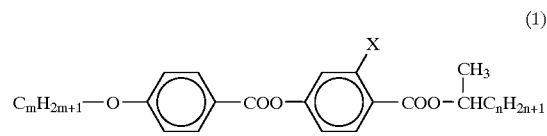

and an anti-ferroelectric liquid crystal composition consisting essentially of said racemic compound and one anti-ferroelectric liquid crystal compound of the formula (2) or a mixture of two or more compounds selected from anti-ferroelectric liquid crystal compounds of the formula (2),

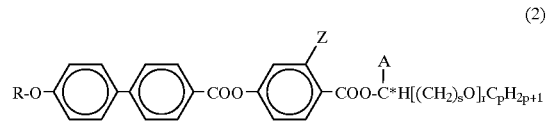

said composition of the present invention, exhibiting a small spontaneous polarization and a fast response so that a display device having a high display quality can be achieved.

9 Claims, 2 Drawing Sheets

FIG. 1

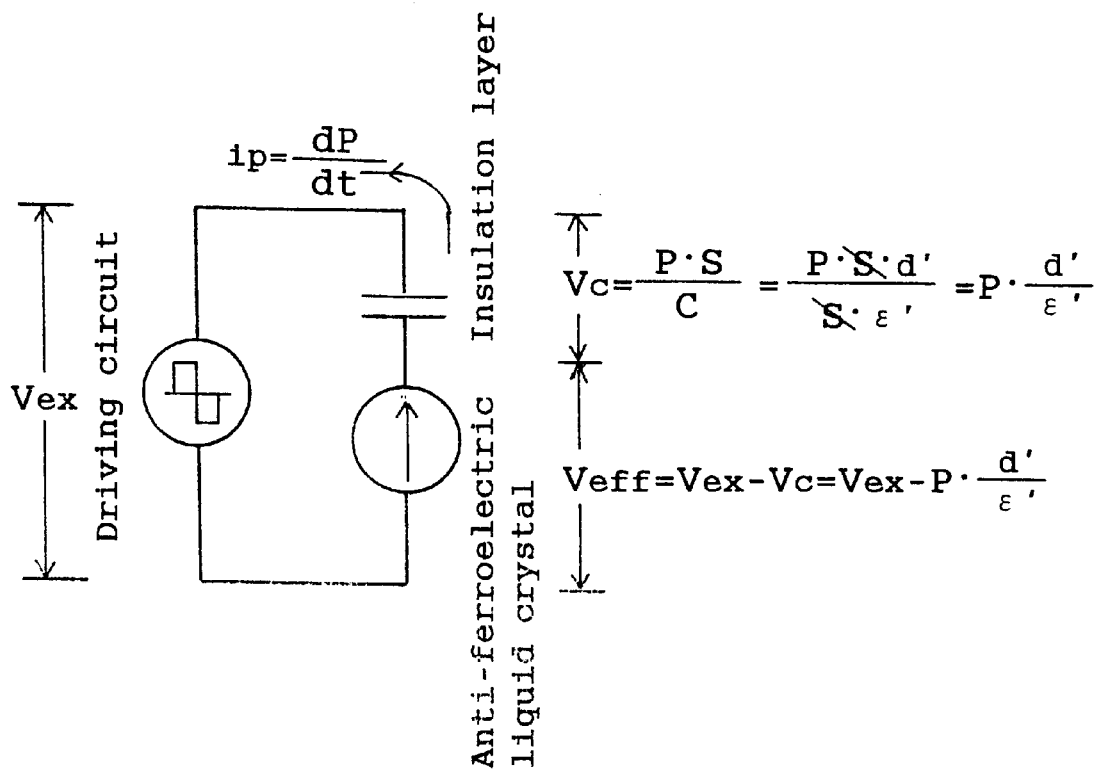

Vex: Drive voltage applied to device

Vc: Voltage generated between the upper and lower surfaces of an alignment layer by the charge of a polarization inversion current Veff: Effective voltatage actually applied to liquid crystal P: Polarization of liquid crystal ip: Polarization inversion current S: Electrode area of liquid crystal device d': Thickness of alignment layer ε': Dielectric constant of alignment layer

RACEMIC COMPOUND AND ANTI-FERROELECTRIC LIQUID CRYSTAL COMPOSITION CONTAINING THE COMPOUND

BACKGROUND OF THE INVENTION (1) Field of the Invention

The present invention relates to a novel racemic compound, a novel anti-ferroelectric liquid crystal composition containing the compound and a liquid crystal display device for which the composition is used.

(2) Description of the Related Art Including Information Disclosed Under 37 CFR 1.97 and 1.98.

A liquid crystal display device has been so far applied to a small-sized display device of various types due to its low-voltage operability, low-power consumption and display capability with a thin screen. Further, the liquid crystal display device is recently practically being applied to the fields of information and office automation-related machines and equipment and the field of television sets, and simultaneously, it is being applied to various fields of other use.

Under the circumstances, energetic developments are under way for attaining a large-sized liquid crystal display device of higher performance that has a higher display capacity and a higher display quality than a conventional CRT display device.

Liquid crystals used in currently available liquid crystal display devices are nematic liquid crystals, and they are classified into simple matrix driven liquid crystal devices and active matrix driven liquid crystal devices according to their driving methods.

Simple matrix driven liquid crystal display devices are produced advantageously in view of a cost due to their simple structures. However, these devices have the problems that the contrast is low due to a cross-talk phenomenon, that driving in a large capacity is difficult and that the display of video frames at a high duty ratio is difficult due to a low response speed. It is therefore necessary to break through many technical problems for attaining a large-sized liquid crystal display device capable of displaying video frames at a high duty ratio.

On the other hand, active matrix driven liquid crystal devices use a TFT (thin film transistor) method as a main stream, but it is required to form thin film transistors for each pixel, and a large investment is required for high production technology and the construction of a production line. The active matrix driving method is therefore far disadvantageous in view of a cost as compared with the simple matrix driving method. However, the active matrix driven liquid crystal device has a high contrast since the cross-talk phenomenon which is a problem of the simple matrix driving method is few, and further, its response speed is high. Therefore, there can be attained a liquid crystal display device which has a high image quality and is capable of displaying video frames at a high duty ratio. For this reason, the TFT method among the active matrix driving methods is gaining its position as a main stream.

At present, large-sized liquid crystal devices having a size of 10 to 20 inches are being developed, while the problem of viewing angle dependency, which is inherent to a device using the nematic liquid crystal, is critically serious. Various technical studies have been made for overcoming the viewing angle dependency, and as a result, displaying with a viewing angle of about 140° has been possible without causing a gray scale inversion. However, the contrast is still dependent greatly upon a viewing angle, and at present, there cannot yet be obtained such flat contrast characteristics with regard to the wide viewing angle as achieved in CRT.

Under the above circumstances, a liquid crystal display device using a ferroelectric liquid crystal attracts attention as a fast response liquid crystal display device. A surface stabilized ferroelectric liquid crystal (SSFLC) device disclosed by Clark and Lagerwall attracts attention due to its high response speed and wide viewing angle which have not been available in the past. Its switching characteristics have been studied in detail, and a number of ferroelectric liquid crystal compounds have been synthesized for optimizing various physical property constants.

On the other hand, for accomplishing a practical device, there have been a number of technical barriers to be overcome such as difficulties in achieving a memory effect and controlling a layer structure due to the difficulty in controlling an alignment, the destruction of an alignment caused by a mechanical shock, and the like, and these problems have been overcome to produce a device as a product.

However, the ferroelectric liquid crystal display device still has problems that it cannot display colors since it cannot handle, in principle, a gray scale and that the display of video frames is difficult because high speed response has not been attained yet.

Further, as another high speed response liquid crystal display device, the development of a device having a switching mechanism different from that of SSFLC is also under way. This is a liquid crystal display device which utilizes switching among tri-stable states of a liquid crystal having an anti-ferroelectric phase (to be referred to as "anti-ferroelectric liquid crystal" hereinafter) (Japanese Journal of Applied Physics, Vol. 27, pp. L729, (1988)).

The anti-ferroelectric liquid crystal has the following three stable states.

That is, the above three stable states are two uniform states (Ur, Ul) observed in two ferroelectric crystal states and one third state. Chandani et al report that the above third state is an anti-ferroelectric phase (Japanese Journal of Applied Physics, vol. 28, pp. L1261 (1989) and Japanese Journal of Applied Physics, vol. 28, pp. L1265 (1989)).

The above switching among the tri-stable states is the first characteristic of an anti-ferroelectric liquid crystal.

The second characteristic of the anti-ferroelectric liquid crystal is that a sharp threshold is present with regard to an applied voltage.

Further, it has a memory effect when a proper bias voltage is set, which is the third characteristic of the anti-ferroelectric liquid crystal.

Further, the fourth characteristic of the anti-ferroelectric liquid crystal is that its layer structure can be easily switched when an electric field is applied (Japanese Journal of Applied Physics, Vol. 28, pp. L119, (1989), and vol. 29, pp. L111 (1990)). Owing to this characteristic, a liquid crystal display device almost free of defects and having self-restoring ability of the alignment can be produced.

By utilizing those characteristics described above, a liquid crystal device having a high response speed and an excellent contrast can be achieved.

Further, it has been demonstrated that the gray shade display, which is almost impossible to achieve with a ferroelectric liquid crystal device, is possible to achieve with an anti-ferroelectric liquid crystal device. It has been consequently made possible to shift toward a full-color display, and the importance of an anti-ferroelectric liquid crystal is further increasing (Preprints of No. 4 Ferroelectric Liquid Crystal International Symposium, page 77, (1993)).

BRIEF SUMMARY OF THE INVENTION

Under the circumstances, energetic developments are under way for achieving an anti-ferroelectric liquid crystal display device, but the developments for achieving practical devices are presently encountering the following problems.

When an anti-ferroelectric liquid crystal is used as a display device, generally, the anti-ferroelectric liquid crystal is sandwiched between two glass substrates coated with an insulation layer and an alignment layer.

The insulation layer is necessary for preventing a short circuit between the substrates, and it is required to have a certain thickness for the complete prevention of a short circuit. On the other hand, the alignment layer is required for aligning liquid crystal molecules in one direction, and it is also required to have a certain thickness for reducing alignment defects, which occur when the liquid crystal molecules are aligned, to the least degree.

When a voltage is applied to the thus formed liquid crystal device, the phase transition from an anti-ferroelectric state to a ferroelectric state occurs sharply with regard to the applied voltage when the insulation layer and the alignment layer have a small thickness or when the insulation layer or the alignment layer is completely absent. However, when the insulation layer and the alignment layer have a certain thickness required for practical use, the phase transition from the anti-ferroelectric state to the ferroelectric state takes place moderately with regard to the applied voltage.

In the driving of an anti-ferroelectric liquid crystal, a holding voltage lower than a writing voltage is continuously applied for a predetermined period of time after the writing voltage for producing a memory effect is applied. When the phase transition from an anti-ferroelectric state to a ferroelectric state takes place moderately with regard to an applied voltage as described above, that is, when a liquid crystal display device has a low steepness of threshold, the holding voltage that can be selected is limited to a very narrow range, and in an extreme case, the holding voltage cannot be set, and no memory effect is secured. This means that an anti-ferroelectric liquid crystal display device is no longer useful as such, which is a serious problem.

Further, the lower the steepness of threshold in the device, the narrower the range of the holding voltage that can be selected, and a so-called driving margin decreases accordingly. A practical device is therefore required to have a high steepness of threshold, and liquid crystal materials which can give such a steepness of threshold are gradually being demanded.

Practically, an anti-ferroelectric liquid crystal is preferably a material that can provide a high steepness of threshold as described above when used in a liquid crystal device.

It has been experimentally found that the steepness of threshold of the liquid crystal device is closely related to the thickness of both the insulation layer and the alignment layer.

Studies have been made to determine what factors can explain the above relationship. In the following studies, both an insulation layer and an alignment layer will be together referred to as an "alignment layer".

For easier understanding of the studies, the studies will be explained with reference to FIGS. 1 to 3 below.

BRIEF DESCRIPTION OF THE SEVERAL VIEWS OF THE DRAWING(S)

FIG. 1 is an equivalent circuit of an anti-ferroelectric liquid crystal device.

DETAILED DESCRIPTION OF THE INVENTION

FIG. 1 shows an equivalent circuit which comprises an electric current source to generate a polarization inversion current according to an applied voltage, an alignment layer that is an electrostatic capacitor C to connect with an anti-ferroelectric liquid crystal in series, and a driving circuit that is an ideal voltage source.

In FIG. 1, the drive voltage applied to a device is taken as Vex, a voltage generated between the upper and lower surfaces of an alignment layer by the charge of a polarization inversion current is taken as Vc, an effective voltage to be actually applied to the liquid crystal is taken as Veff, a spontaneous polarization of the liquid crystal is taken as P, an electrode area of the liquid crystal device is taken as S, a thickness of the alignment layer is taken as d', and a dielectric constant of the alignment layer is taken as $\epsilon'$. Vc is calculated as in the following equation (1).

$$Vc = PS/C = PSd'/(S\epsilon') = P(d'/\epsilon') \tag{1}$$

On the basis of the above equation, Veff is expressed as in the following equation (2).

$$Veff = Vex - Vc = Vex - P(d'/\epsilon') \tag{2}$$

As is clear from the equation (2), the voltage actually applied to the liquid crystal is lower than the externally applied voltage by a product of the polarization P of the liquid crystal, the thickness d' of the alignment layer and a reciprocal number $1/\epsilon'$ of the dielectric constant of the alignment layer.

Then, when a thickness of the liquid crystal layer filled in a liquid crystal cell is taken as d, an electric field Eeff actually applied to the liquid crystal is expressed by the following equation (3).

$$Eeff = Veff/d \tag{3}$$

On the other hand, an apparent electric field strength Eex is expressed by the following equation (4).

$$Eex = Vex/d = (Veff + Vc)/d = Veff/d + P(d'/\epsilon')/d = Eeff + \alpha P \tag{4}$$

wherein $$\alpha = d'/(\epsilon' d) \tag{5}$$

When no alignment layer is present, the second term in the equation (4) is 0, and hence Eex=Eeff.

Figure 2:
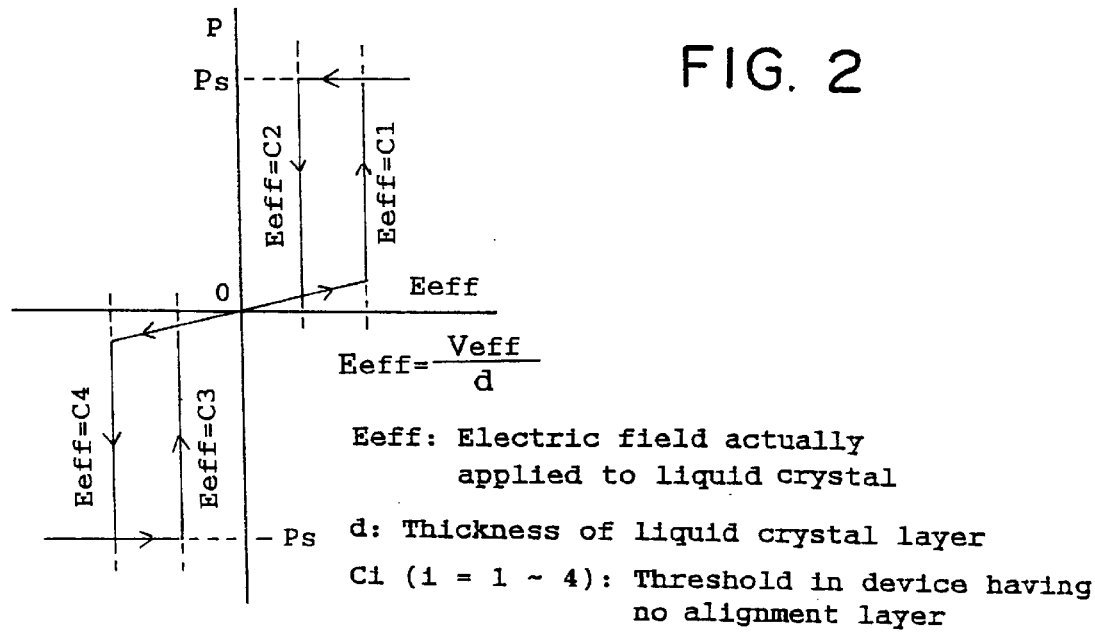
FIG. 2 shows a simulation result on the steepness of threshold when alignment layer is present.

While an anti-ferroelectric liquid crystal shows a hysteresis of its optical response with regard to an applied voltage, four thresholds are thinkable with regard to the hysteresis. Each threshold is Eeff (=Eex), and in this case, these thresholds do not incline to an electric field. FIG. 2 shows this appearance.

When an alignment layer is present, the equation (4) is modified to obtain the following equation (6).

$$Eeff = Eex - \alpha P \tag{6}$$

Figure 3:
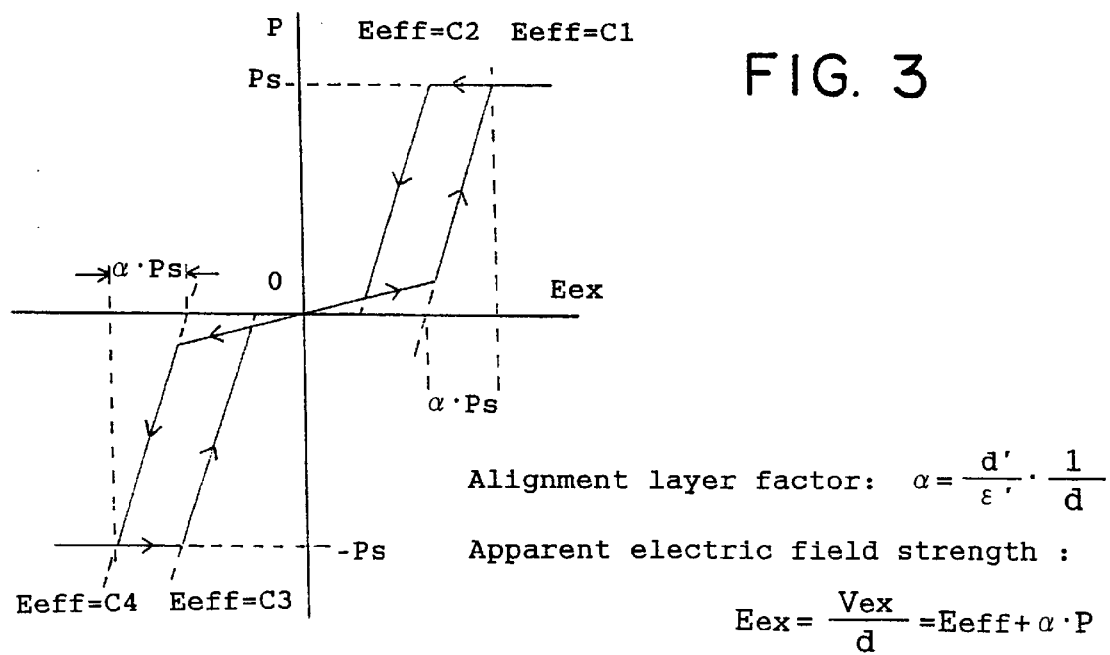
FIG. 3 shows a simulation result on the steepness of threshold when an alignment layer is present.

That is, an effective electric field exerting on the liquid crystal is lower than the applied electric field Eex by $\alpha \cdot P$. As a result, the hysteresis is strained to a great extent due to the contribution of the $\alpha \cdot P$ as shown in FIG. 3.

The above studies show that the strain of hysteresis is greatly caused by the interaction of the spontaneous polarization and the alignment layer. For obtaining a liquid crystal device having the reduced strain of hysteresis, therefore, it is effective to decrease the above interaction so as to make it as small as possible.

The measures that can be specifically taken for achieving the above purpose include a means to use an alignment layer having a high dielectric constant, a means to decrease the thickness of the alignment layer or to decrease the spontaneous polarization of the liquid crystal, as is clear from the above equations (5) and (6). Of the above measures, it is rather difficult to acquire an alignment layer material having a high dielectric constant and hence, the measures that can be practically taken is a means to decrease the thickness of the alignment layer or to decrease the spontaneous polarization of the liquid crystal material.

Generally, an anti-ferroelectric liquid crystal compound has a considerably large spontaneous polarization, and a liquid crystal material having relatively excellent physical properties has a spontaneous polarization of 200 nC/cm$^2$ or more. Therefore, unless the thickness of the alignment layer is much decreased, the strain of the hysteresis is considerably large. However, when the thickness of the alignment layer is decreased, there occurs a problem that the alignment state of the liquid crystal molecules is too defective to procure a contrast. The measure for correcting the strain of the hysteresis by decreasing the thickness of the alignment layer is therefore considerably limited.

On the other hand, in order to decrease the spontaneous polarization of a liquid crystal material, it is inevitable to take a means to mix a proper compound having no spontaneous polarization with the liquid crystal material, that is, to dilute the liquid crystal material to decrease its concentration. Since, however, the response speed of a liquid crystal is determined by a product of an applied voltage and a spontaneous polarization, there occurs another new problem that the response speed decreases when the spontaneous polarization is decreased simply by mixing with a proper compound.

Under the circumstances, for obtaining a device having a decreased strain of hysteresis, attempts have been so far made to develop an anti-ferroelectric liquid crystal having a low spontaneous polarization, a low threshold voltage and a low viscosity, but it is a current situation that no satisfactory achievements have been obtained.

The present invention has been made from the above points of view, and has been completed by finding the following. By selecting and adding a racemic compound having a novel chemical structure to an anti-ferroelectric liquid crystal, the spontaneous polarization can be decreased without decreasing the response speed, and when the composition is used for forming a liquid crystal device, a liquid crystal device having a decreased strain of hysteresis can be obtained.

That is, according to the present invention, there is provided a racemic compound of the following general formula (1),

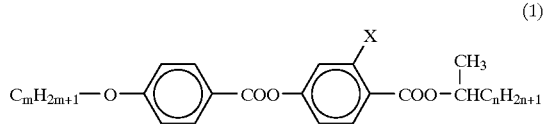

wherein m is an integer of 8 to 10, n is an integer of 3 to 8, and X is a hydrogen atom or a fluorine atom.

Further, according to the present invention, there is provided an anti-ferroelectric liquid crystal composition consisting essentially of one or more of the racemic compound of the following general formula (1)

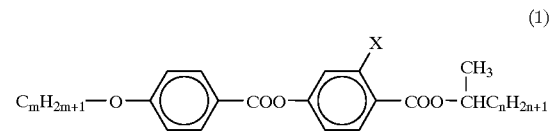

wherein m is an integer of 8 to 10, n is an integer of 3 to 8, and X is a hydrogen atom or a fluorine atom, and an anti-ferroelectric liquid crystal compound of the following formula (2),

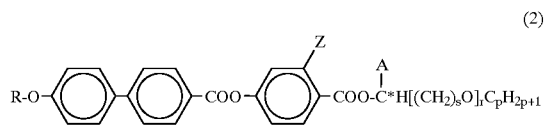

wherein R is a linear alkyl group having 6 to 12 carbon atoms, Z is a hydrogen atom or a fluorine atom, A is —CH$_3$ or —CF$_3$, r is 0 or 1 and C* is an asymmetric carbon atom, provided that when A is —CH$_3$, r is 0 and p is an integer of 4 to 10, that when A is —CF$_3$ and r is 0, p is an integer of 6 to 8 and that when A is —CF$_3$ and r is 1, s is an integer of 5 to 8 and p is an integer of 2 or 4.

The present invention will be more specifically explained hereinafter.

In the above general formula (1) for the racemic compound of the present invention, m is an integer of 8 to 10, preferably 9, and n is an integer of 3 to 8, preferably 6. Further, X is a hydrogen atom or a fluorine atom, preferably a fluorine atom.

The racemic compound of the above general formula (1) can be produced by the following method, for example.

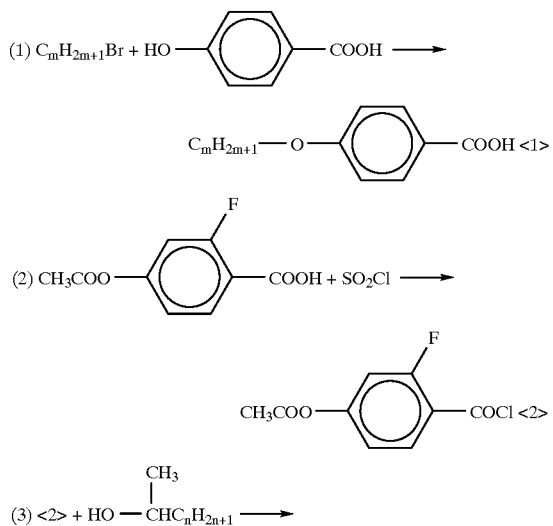

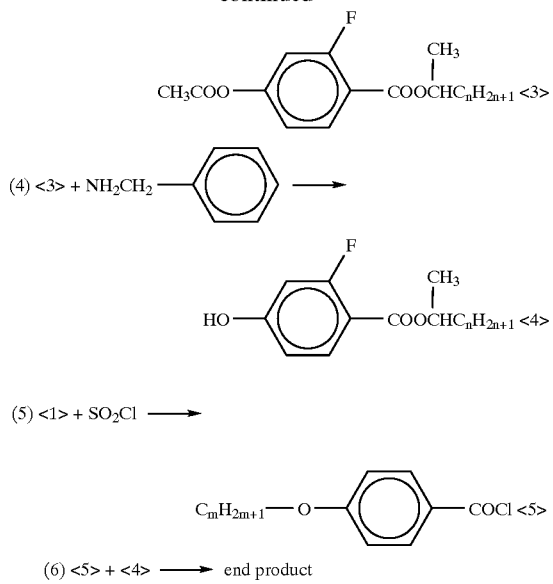

The production method of the racemic compound of the above general formula will be briefly explained below.

(1) shows the etherfication by the reaction of alkyl bromide and 4-hydroxybenzoic acid.

(2) shows the conversion of 4-acetoxy-2-fluorobenzoic acid to chloride.

(3) shows the esterification by the reaction of acid chloride and 2-alkyl alcohol.

(4) shows deacetylation.

(5) shows the conversion of p-alkoxybenzoic acid to chloride.

(6) shows an esterification with acid chloride (formation of an end product).

The anti-ferroelectric liquid crystal composition consists essentially of the racemic compound of the general formula (1) and the anti-ferroelectric liquid crystal compound of the general formula (2).

In the general formula (2), R is a linear alkyl group having 6 to 12 carbon atoms, preferably 8 to 10 carbon atoms, Z is a hydrogen atom or a fluorine atom, A is a —$CH_3$ or —$CF_3$, and r is 0 or 1. Further, the definitions of p and s vary depending upon the kind of A and the value of r. That is, when A is —$CH_3$, r is 0 and p is an integer of 4 to 10. When A is —$CF_3$ and r is 0, p is an integer of 6 to 8. When A is —$CF_3$ and r is 1, s is an integer of 5 to 8 and p is an integer of 2 or 4.

As a compound of the general formula (2), preferred are a compound of the general formula (2) in which A is —$CF_3$ and r is 1 and a compound of the general formula (2) in which A is —$CH_3$, r is 0 and p is an integer. of 4 to 6.

The anti-ferroelectric liquid crystal compound of the general formula (2) can be easily produced, for example, by the following method. A compound of the general formula (2) in which A=—$CF_3$, p=2, r=1 and s=5 is produced by the following method.

(a) AcO—Ph(Z)—COOH+$SOCl_2$→AcO—Ph(Z)—COCl (b) (a)+HOC*H($CF_3$)($CH_2$)$_5$O$C_2H_5$→AcO—Ph(Z)—COOC*H($CF_3$)($CH_2$)$_5$O$C_2H_5$ (c) (b)+Ph—$CH_2NH_2$→HO—Ph(Z )—COOC*H (CF$_3$)($CH_2$)$_5$O$C_2H_5$ (d) RO—Ph—Ph—COOH+$SOCl_2$→RO—Ph—Ph—COCl (e) (b)+(d)→anti-ferroelectric liquid crystal compound In the above formulae, AcO— is an acetyl group, —Ph(Z)— is a 1,4-phenylene group in which fluorine may be substituted, Ph— is a phenyl group, —Ph— is a 1,4-phenylene group and C* is an asymmetric carbon atom.

The above production method will be briefly explained below.

(a) shows the chlorination of fluorine-substituted or non-substituted p-acetoxybenzoic acid with thionyl chloride.

(b) shows a reaction between a chlorination product obtained in (a) and an alcohol to form an ester.

(c) shows the deacetylation of the ester obtained in (b).

(d) shows the chlorination of 4'-alkyloxybiphenyl-4-carboxylic acid.

(e) shows the formation of a liquid crystal by a reaction between a phenol obtained in (c) and a chlorination product obtained in (d).

The anti-ferroelectric liquid crystal composition of the present invention consists essentially of the racemic compound of the above general formula (1) and the anti-ferroelectric liquid crystal compound of the general formula (2). Specifically, it is advantageous that the total amount of the compounds of the formulae (1) and (2) based on the total composition is at least 70 mol %, preferably at least 80 mol %.

The mixing ratio ((1):(2))of the compound of the above general formula (1) to the compound of the above general formula (2) is preferably in the range of 1:99 to 40:60, particularly preferably 5:95 to 35:65, in terms of a molar ratio.

Further, a compound or a mixture of at least two compounds of the above general formula (2) may be used. The use of a mixture of at least two compounds of the formula (2) can give a liquid crystal display device which is excellent in alignment characteristic and steepness of threshold and exhibits a high contrast.

In the anti-ferroelectric liquid crystal composition of the present invention, preferably, the upper limit of temperature range of the anti-ferroelectric phase is at least 40° C., the lower limit thereof is 0° C. or lower, and at least a smectic A phase is present outside a temperature range higher than the temperature range in which the anti-ferroelectric phase is present. The anti-ferroelectric liquid crystal composition of the present invention is preferably used in an anti-ferroelectric liquid crystal display device formed by interposing the composition between a pair of electrode substrates.

The present invention can provide a novel racemic compound and a novel anti-ferroelectric liquid crystal composition containing the above racemic compound. Further, the novel anti-ferroelectric liquid crystal composition of the present invention can provide an anti-ferroelectric liquid crystal display device which is excellent in steepness of threshold, has an anti-ferroelectric phase over a broad temperature range and exhibits a high speed response, and which therefore has a high display quality.

EXAMPLES

The present invention will be explained more specifically with reference to Examples and Comparative Examples hereinafter, while the present invention shall not be limited thereto.

Example 1

Preparation of 3-fluoro-4-(1-methylheptyloxycarbonyl)phenyl=4-n-nonyloxybenzoate (Formula (1): m=9, n=6, X=F (E1))

(1) Preparation of p-nonyloxybenzoic acid 12.7 Grams (0.0917 mol) of p-hydroxybenzoic acid, 28.5 g of n-nonyl bromide and 10.2 g of potassium hydroxide were added to a mixture composed of 1,500 ml (milliliter) of ethanol and 200 ml of water, and the mixture was allowed to react under reflux for 10 hours. Further, 500 ml of water was added thereto, and the mixture was stirred for 3 hours. After the completion of the reaction, a concentrated hydrochloric acid was added to acidify the reaction mixture. Thereafter, the solvent was distilled off, and the remaining product was cooled to room temperature and then filtered to give a colorless solid. The solid was fully washed with water and re-crystallized from chloroform to give an intended product (yield 75%).

(2) Preparation of 4-acetoxy-2-fluoro-1-(1-methylheptyloxycarbonyl)benzene

To 10.8 g (0.06 mol) of 4-acetoxy-2-fluorobenzoic acid was added 60 ml of thionyl chloride, and the mixture was allowed to react under reflux for 7 hours. Then, excess thionyl chloride was distilled off, and 10 ml of pyridine and 5.3 g (0.0402 mol) of 2-octanol were added dropwise. The resultant mixture was stirred at room temperature for a whole day, and then diluted with 200 ml of ether. An organic layer was washed with dilute hydrochloric acid, with a 1N sodium hydroxide aqueous solution and with water in this order, and dried over magnesium sulfate.

The solvent was distilled off, and the resultant crude intended product was purified with silica gel column chromatograph using hexane/ethyl acetate as solvents, to give an intended product (yield 90%).

(3) Preparation of 2-fluoro-4-hydroxy-1-(1-methylheptyloxycarbonyl)benzene 9.7 Grams (0.0361 mol) of the compound obtained in the above (2) was dissolved in 250 ml of ethanol, and 7.7 g (0.0772 mol) of benzylamine was added dropwise. Further, the mixture was stirred at room temperature for a whole day and diluted with 300 ml of ether, and the diluted mixture was washed with dilute hydrochloric acid and with water in this order, and dried over magnesium sulfate. The solvent was distilled off, and an intended product was isolated and purified by silica gel column chromatography (yield 98%).

(4) Preparation of 3-fluoro-4-(1-methylheptyloxycarbonylphenyl)=4-n-nonyloxybenzoate To 3.1 ml of the compound obtained in the above (1) was added 15 ml of thionyl chloride, and the mixture was refluxed under heat for 5 hours. Excess thionyl chloride was distilled off, then, 2 ml of pyridine and 2.12 mmol of the compound obtained in the above (3) were added, and the mixture was allowed to react at room temperature for 10 hours.

After the completion of the reaction, the reaction mixture was diluted with 300 ml of ether, the diluted mixture was washed with dilute hydrochloric acid, with a 1N sodium carbonate aqueous solution and with water in this order, and an organic layer was dried over magnesium sulfate.

Then, the solvent was distilled off, and an intended product was isolated by silica gel column chromatography (yield 81%).

Table 1 shows NMR data of the compound obtained in Example 1, and the formula of the compound is shown as the formula, (E1).

TABLE 1

| | Chemical shift | | | | | | |
|---|---|---|---|---|---|---|---|
| | 1H | 2H | 3H | 4H | 5H | 6H | 7H |
| Example 1 (E1) | 4.1 | 7.0 | 7.1 | 7.1 | 7.1 | 8.0 | 5.2 |

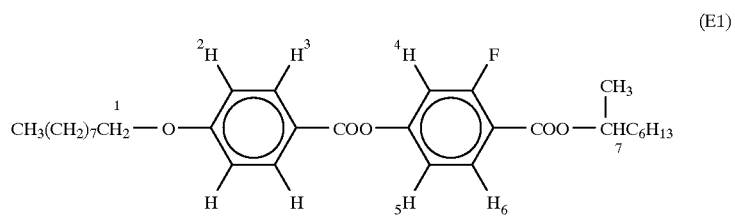

(E1)

Comparative Example 1

Anti-ferroelectric liquid crystal compounds (2A and 2B) of the following formulae were mixed in a mixing ratio of 70/30 (molar ratio) to obtain an anti-ferroelectric liquid crystal composition.

Table 2 shows the phase sequence of the obtained composition. Further, the liquid crystal composition was measured for a spontaneous polarization at 60° C. and a response time in the transition from an anti-ferroelectric state to a ferroelectric state. Table 2 shows the results.

2A: $C_9H_{19}O$—Ph—Ph—COO—Ph(3F)—COO—C*H$(CF_3)(CH_2)_5OC_2H_5$ (Formula (2): R=$C_9H_{19}$, Z=F, A=$CF_3$, r=1, s=5 and p=2)

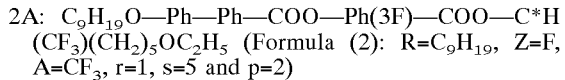

2B: $C_8H_{17}O$—Ph—Ph—COO—Ph(3F)—COO—C*H$(CH_3)C_5H_{11}$ (Formula (2): R=$C_8H_{17}$, Z=F, A=$CH_3$, r=0 p=5)

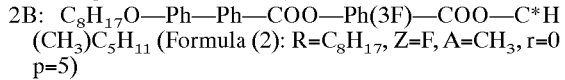

The above composition was measured or evaluated for an optical response hysteresis, a response time and a spontaneous polarization as follows.

A liquid crystal cell (cell thickness 2 μm) having ITO electrodes and a rubbed polyimide thin film (30 nm) was charged with a liquid crystal composition in an isotropic state. Then, the cell was gradually cooled at a rate of 1.0° C./minute to align the liquid crystal. The cell was interposed between the crossed polarizers such that the layer direction of the liquid crystal was in parallel with an analyzer or a polarizer.

The response time in a transition from an anti-ferroelectric state to a ferroelectric state was defined to be an amount of time required for a change in transmittance from 10% to 90% when a maximum transmittance represented 100%, and a minimum transmittance represented 0%, under the application of 25 V having a frequency of 10 Hz at 60° C.

The spontaneous polarization was determined by applying a 25 V triangular wave at 60° C. and measuring a polarization inversion current.

Example 2

The anti-ferroelectric liquid crystal composition containing the anti-ferroelectric liquid crystal compounds (2A and 2B), used in Comparative Example 1, was mixed with the racemic compound (E1) obtained in Example 1 in a 2A/2B/E1 mixing ratio of 56/24/20 (molar ratio), to obtain an anti-ferroelectric liquid crystal composition. The so-obtained composition was measured or evaluated for a phase sequence, a spontaneous polarization and a response time in the same manner as in Comparative Example 1. Table 2 shows the results.

Though the spontaneous polarization was decreased, a higher response capability was exhibited.

TABLE 2

| | Phase sequence | Spontaneous polarization (nC/cm$^2$) | Response time ($\mu$second) |
|---|---|---|---|
| Ex. 2 | Cr(<−20)SCA*(76)SA(92)I | 116 | 38 |
| C Ex. 1 | Cr(<−10)SCA*(95)SC*(97)SA(105)I | 172 | 53 |

Ex. = Example, C Ex. = Comparative Example

In the phase sequence, parenthesized values show transition temperatures (°C.), Cr is a crystal phase, SCA* is an anti-ferroelectric phase, SC* is a ferroelectric phase, SA is a smectic A phase, and I is an isotropic phase.

What is claimed is:

1. An anti-ferroelectric liquid crystal composition consisting essentially of one or more of a racemic compound of the general formula (1),

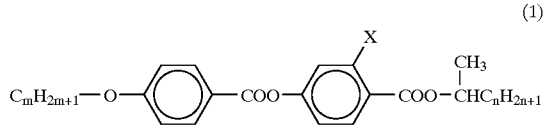
(1)

wherein m is an integer of 8 to 10, n is an integer of 3 to 8, and X is a hydrogen atom or a fluorine atom, and an anti-ferroelectric liquid crystal compound of the following formula (2),

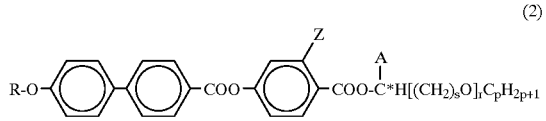
(2)

wherein R is a linear alkyl group having 6 to 12 carbon atoms, Z is a hydrogen atom or a fluorine atom, A is —CH$_3$ or —CF$_3$, r is 0 or 1 and C* is an asymmetric carbon atom, provided that when A is —CH$_3$, r is 0 and p is an integer of 4 to 10, that when A is —CF$_3$ and r is 0, p is an integer of 6 to 8 and that when A is —CF$_3$ and r is 1, s is an integer of 5 to 8 and p is an integer of 2 or 4.

2. The composition of claim 1, wherein m in the general formula (1) is 9.

3. The composition of claim 1, wherein n in the general formula (1) is 6.

4. The composition of claim 1, wherein X in the general formula (1) is a fluorine atom.

5. The composition of claim 1, wherein in the general formula (2), A is —CH$_3$, r is 0 and p is an integer of 4 to 6.

6. The composition of claim 1, wherein the composition contains the racemic compound of the general formula (1) and the anti-ferroelectric liquid crystal compound of the general formula (2) in a molar ratio ((1):(2)) of 1:99 to 40:60.

7. The composition of claim 1, wherein an upper limit of temperature range of an anti-ferroelectric phase of the composition is at least 40° C., a lower limit thereof is 0° C. or lower, and at least a smectic A phase is present outside a temperature range higher than the temperature range in which the anti-ferroelectric phase is present.

8. Anti-ferroelectric liquid crystal display device comprising the anti-ferroelectric liquid crystal composition recited in claim 1, which is interposed between a pair of electrode substrates.

9. An anti-ferroelectric liquid crystal composition consisting essentially of one or more of a racemic compound of the general formula (1),

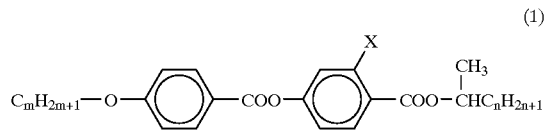
(1)

wherein
m is an integer of 8 to 10,
n is an integer of 3 to 8, and
X is a hydrogen atom or a fluorine atom and
an anti-ferroelectric liquid crystal compound of the following formula (2)

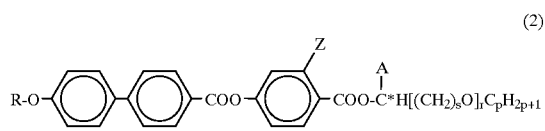
(2)

wherein
R is a linear alkyl group having 6 to 12 carbon atoms,
Z is a hydrogen atom or a fluorine atom,
A is —CF$_3$,
r is 1,
C* is an asymmetric carbon atom
s is an integer of 5 to 8, and
p is an integer of 2 or 4.

* * * * *